United States Patent [19]

Tsunoda et al.

[11] 4,016,352
[45] Apr. 5, 1977

[54] 2,3-O-SULFINYL-CYTIDINE-5-PHOSPHATE

[75] Inventors: Kozo Tsunoda; Tsuneo Sowa; Kiyohide Sako, all of Miyazaki, Japan

[73] Assignee: Asahi Kasei Kogyo Kabushiki Kaisha, Osaka, Japan

[22] Filed: Mar. 13, 1975

[21] Appl. No.: 558,098

[30] Foreign Application Priority Data

Dec. 27, 1974 Japan .................................49-148936

[52] U.S. Cl. .......................... 536/29; 260/256.4 E; 260/256.4 F; 260/256.4 H; 260/256.5 R; 424/180

[51] Int. Cl.$^2$ ....................... C07H 19/10

[58] Field of Search ............ 260/256.4 H, 256.4 E, 260/211.5 R

[56] References Cited

UNITED STATES PATENTS 3,322,747 5/1967 Shen et al. .................. 260/211.5 R
3,894,000 7/1975 Wechter et al. ............ 260/211.5 R

OTHER PUBLICATIONS

Sowa, et al., "Chemical Abstracts", vol. 78, 1973, col. 587556.

*Primary Examiner*—Donald G. Daus
*Assistant Examiner*—James H. Turnipseed
*Attorney, Agent, or Firm*—Sughrue, Rothwell, Mion, Zinn & Macpeak

[57] ABSTRACT

A process for preparing 2,2'-anhydrocytidine-5'-phosphate having an antitumor activity for cytidine-5'-phosphate which comprises heating a novel intermediate 2',3'-O-sulfinylcytidine-5'-phosphate in water, an aprotonic polar solvent or a cyclic tertiary amine, and a novel intermediate, 2',3'-O-sulfinyl-cytidine-5'-phosphate represented by the formula (I)

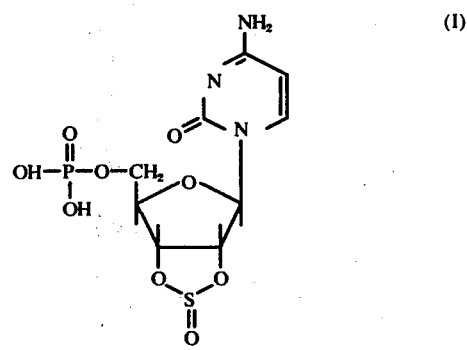

and a process for preparing the intermediate 2',3'-O-sulfinyl-cytidine-5'-phosphate which comprises reacting cytidine-5'-phosphate with a thionyl halide in a polar organic solvent in the presence of a cyclic tertiary amine.

1 Claim, 4 Drawing Figures

2,3-O-SULFINYL-CYTIDINE-5-PHOSPHATE

BACKGROUND OF THE INVENTION

1. Field of the Invention

This invention relates to a process for preparing 2,2'-anhydrocytidine-5'-phosphate having an antitumor activity and, more particularly, it relates to a process for preparing 2,2'-anhydrocytidine-5'-phosphate in high yield via a novel intermediate 2',3'-O-sulfinyl-cytidine-5'-phosphate from cytidine-5'-phosphate. The present invention also relates to a novel intermediate, 2',3'-O-sulfinyl-cytidine-5'-phosphate represented by the formula (I)

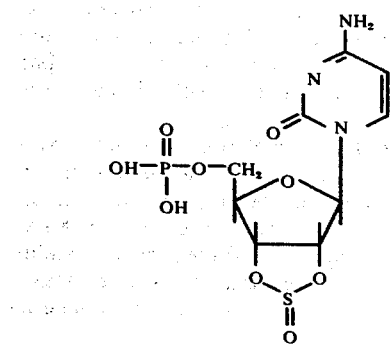

(I)

and a process for preparing 2',3'-O-sulfinyl-cytidine-5'-phosphate which comprises reacting cytidine-5'-phosphate with a thionyl halide in a polar organic solvent in the presence of a cyclic tertiary amine.

2. Description of the Prior Art

It is well known that 2,2'-anhydrocytidine-5'-phosphate per se possesses an antitumor activity as reported in Gann., 64, 519–522 (1973), Japan, and is also expected to have an anti-leukemia activity which is useful as a chemotherapy agent for treating and alleviating the leukemia.

Hitherto, various processes have been proposed for preparing 2,2'-anhydrocytidine-5'-phosphate such as a process comprising a specific phosphorylation of 2,2'-anhydrocytidine-5'-phosphate as proposed by the present inventors disclosed in Japanese patent application OPI No. 5997/1974, a process comprising heat-reacting cytidine-5'-phosphate in the presence of a large excess of a partially hydrolyzed phosphorus oxychloride in ethyl acetate as reported by T. Kanai et al., Tetrahedron Letters, 22, 1965-1968 (1971), etc. However, these prior art processes have serious disadvantages in that they require a large excess of phosphorus oxychloride which results in the formation of a large amount of undesirable inorganic acids and inorganic salts as by-products and that 2,2'-anhydrocytidine-5'-phosphate is easily decomposed into (1-β-D-arabinofuranosyl)cytidine-5'-phosphate since 2,2'-anhydrocytidine-5'-phosphate is extremely unstable under alkaline conditions, and thus the above conventional processes necessitate markedly complicated and cumbersome procedures in purifying and isolating the desired product and also a large amount of expensive reagents.

For the above reasons, these conventional processes are not considered to be appropriate for the production of 2,2'-anhydrocytidine-5'-phosphate on an industrial scale.

SUMMARY OF THE INVENTION

It has not been found in accordance with the present invention that 2,2'-anhydrocytidine-5'-phosphate of the formula (II)

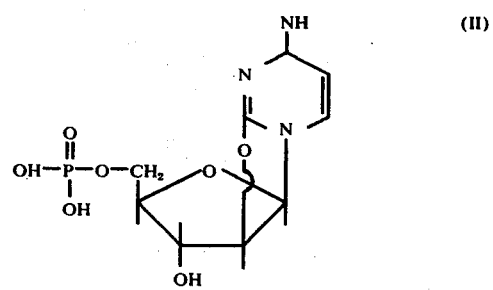

(II)

can be prepared in high yields by heating a novel intermediate 2',3'-O-sulfinyl-cytidine-5'-phosphate of the formula (I)

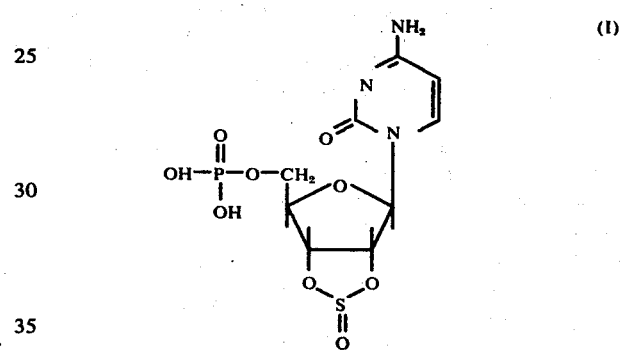

(I)

in a solvent which is selected from water, an aprotonic polar solvent and a cyclic tertiary amine.

A primary object of the present invention is therefore to provide a process for preparing 2,2'-anhydrocytidine-5'-phosphate from cytidine-5'-phosphate via a novel intermediate 2',3'-O-sulfinyl-cytidine-5'-phosphate.

Another object of this invention is to provide a novel intermediate 2',3'-O-sulfinyl-cytidine-5'-phosphate which is capable of producing the desired 2,2'-anhydrocytidine-5'-phosphate in high yield by a simple and economical procedure.

A further object of this invention is to provide a process for preparing a novel intermediate 2',3'-O-sulfinyl-cytidine-5'-phosphate.

BRIEF DESCRIPTION OF THE ACCOMPANYING DRAWINGS

DETAILED DESCRIPTION OF THE INVENTION

Figure 1:
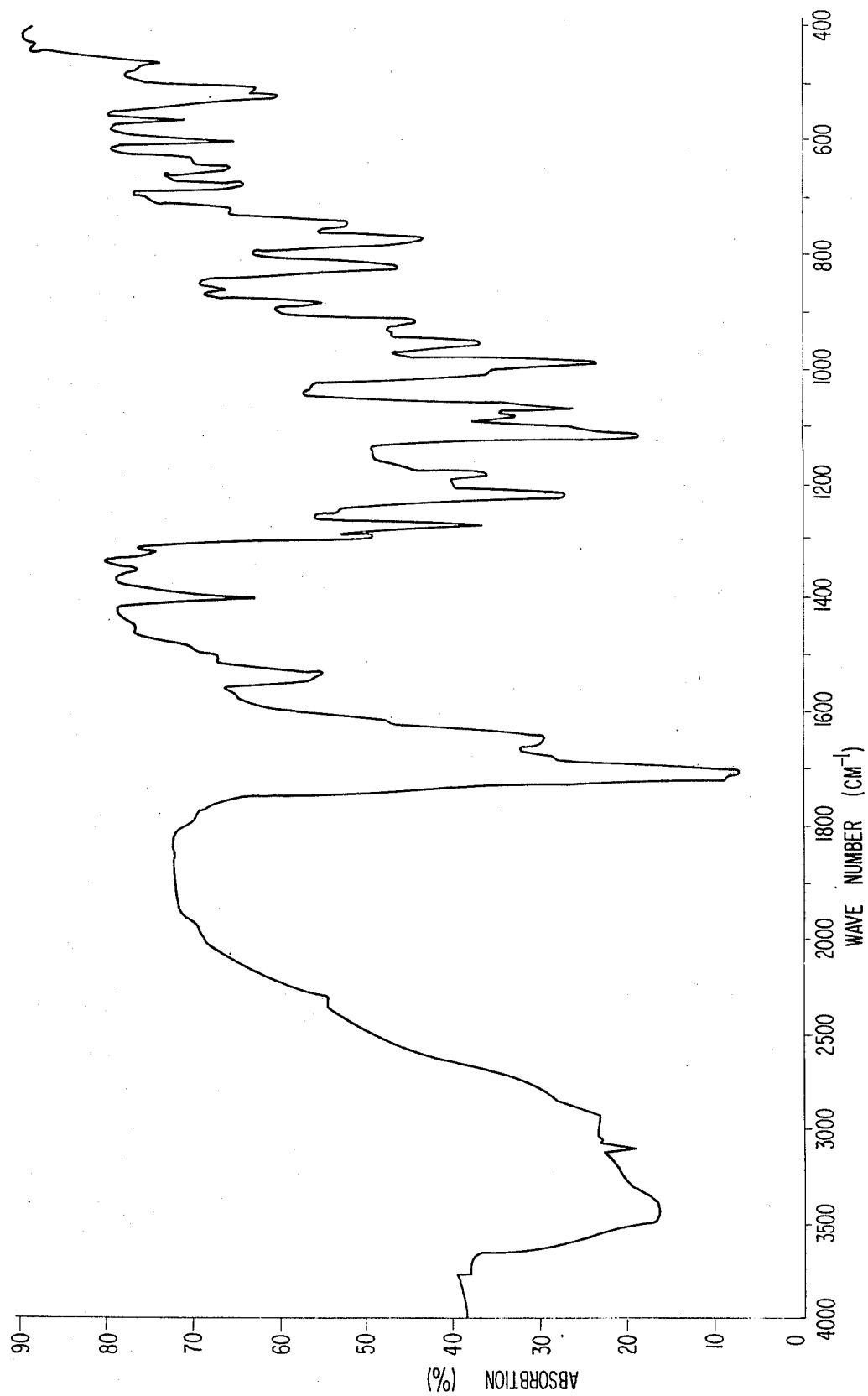
FIG. 1 is an IR absorption spectrum of 2',3'-O-sulfinyl-cytidine-5'-phosphate.
Figure 2:
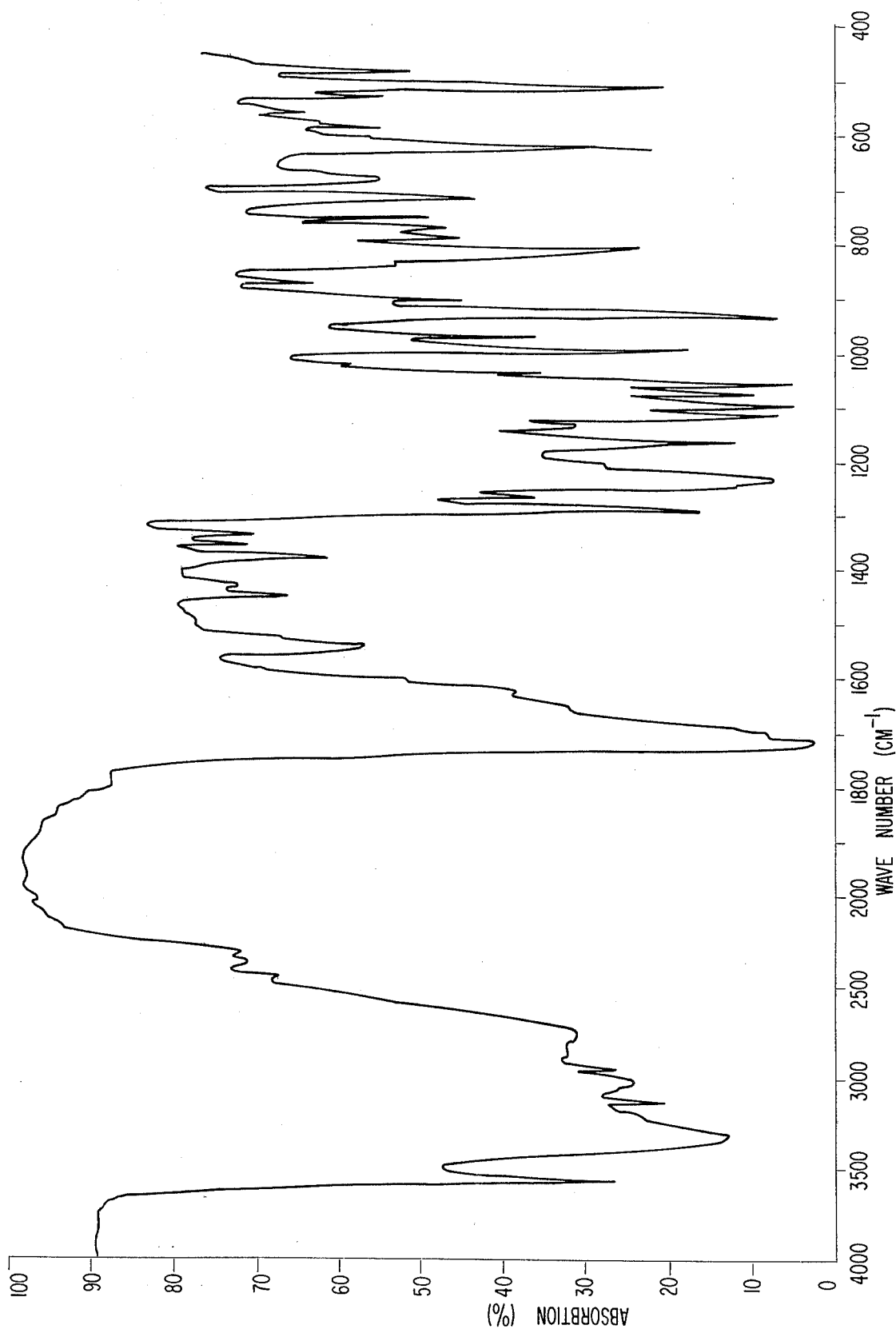
FIG. 2 is an IR absorption spectrum of cytidine-5'-phosphate as a reference.

The 2',3'-O-sulfinyl-cytidine-5'-phosphate which is an intermediate of the present invention can be produced by reacting cytidine-5'-phosphate of the formula (III)

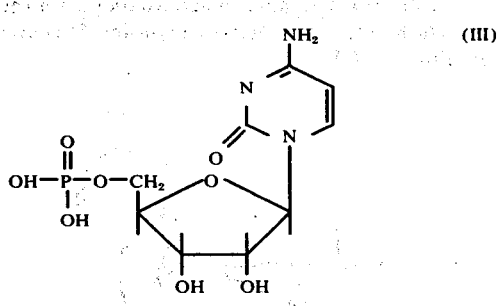

with a thionyl halide, for example, thionyl chloride, in a polar organic solvent in the presence of a cyclic tertiary amine. The thionyl halide can be used in an amount of at least 1 mole, preferably 2 to 10 moles, per mole of the starting cytidine-5'-phosphate. Although the use of a large excess of the thionyl halide does not adversely affect the reaction and the desired product, the use of the excess amount is not preferred since it makes the purification and isolation of the desired intermediate 2',3'-O-sulfinyl-cytidine-5'-phosphate difficult and further the expensive thionyl halide is consumed uneconomically.

The polar organic solvents which can be used as a reaction medium in the preparation of 2',3'-O-sulfinyl-cytidine-5'-phosphate include nitrile compounds such as acetonitrile, propionitrile; nitro compounds such as nitromethane, nitroethane; cyclic ether compounds such as dioxane, tetrahydrofuran; cyclic tertiary amines such as pyridine, α-picoline, β-picoline, γ-picoline, 2,6-lutidine; and aprotonic polar solvents such as dimethylformamide, dimethylacetamide, dimethylsulfoxide, hexamethylphosphoramide.

The amount of the polar organic solvents used in the present invention can be about at least 0.5 liters, preferably less than about 4 liters, per mole of the starting cytidine-5'-phosphate. When the amount of the polar organic solvents is less than about 0.5 liters per mole of the cytidine-5'-phosphate, not only the viscosity of the reaction solution increases but also a large amount of by-products is disadvantageously formed since it is impossible to control a rapid rising of the reaction temperature.

In the process of this invention, the cyclic tertiary amines are used to increase the solubility of the starting cytidine-5'-phosphate in the reaction medium and to ensure a smooth reaction.

Suitable example of the cyclic tertiary amines which can be used in the present invention include pyridine, α-picoline, β-picoline, γ-picoline and 2,6-lutidine.

The amount of the cyclic tertiary amine is not critical, but it has been found that the amount of at least about 2 moles, preferably more than 2.5 moles, per mole of the starting cytidine-5'-phosphate can be advantageously used. These cyclic tertiary amines can be used in any large excess amount relative to the starting cytidine-5'-phosphate and can be served as a reaction medium. For example, pyridine as a cyclic tertiary amine can be used in an excess amount to eliminate the necessity of a polar organic solvent.

In carrying out the process of this invention, the polar organic solvent, the cyclic tertiary amine and the starting cytidine-5'-phosphate can be combined in any order, but in order to avoid a possible heat-decomposition of the starting cytidine-5'-phosphate and 2',3'-O-sulfinyl-cytidine-5'-phosphate produced in the reaction due to the exothermic reaction between the thionyl halide and the cyclic tertiary amine, it is preferred that the thionyl halide and the cyclic tertiary amine are first combined with the polar organic solvent followed by cooling the resulting mixture and then cytidine-5'-phosphate is added to the resulting mixture while maintaining the reaction mixture at an appropriate temperature.

The reaction temperature is typically in the range of from about −20° to +30° C. Temperatures lower than about −20° C can be used but generally tend to prolong the reaction time and are not preferable from the practical standpoint. When the reaction is carried out at a temperature above about 30° C, especially above about 50° C, the 2',3'-O-sulfinyl-cytidine-5'-phosphate formed are decomposed thereby resulting in the formation of by-products.

The time required for completing the reaction varies depending upon other reaction parameters such as the amount of the thionyl halide and the cyclic tertiary amines, the reaction temperature used and the type of the polar organic solvent used as the reaction medium. It has been found, however, that the reaction time of from about 30 minutes to about 3 hours is generally sufficient.

The intermediate 2',3'-O-sulfinyl-cytidine-5'-phosphate can be isolated from the reaction mixture by usual procedures which are well known to one skilled in the art, for example, by combining the reaction mixture with ice-water to decompose any remaining unreacted thionyl halide and adjusting the resulting mixture to a pH of about 1 to about 2.5 to precipitate the desired 2',3'-O-sulfinyl-cytidine-5'-phosphate which is then isolated and purified, or adding a water-soluble organic solvent such as ethanol to the above hydrolyzed reaction mixture to precipitate the desired 2',3'-O-sulfinyl-cytidine-5'-phosphate which is then isolated and purif ed.

Figure 3:
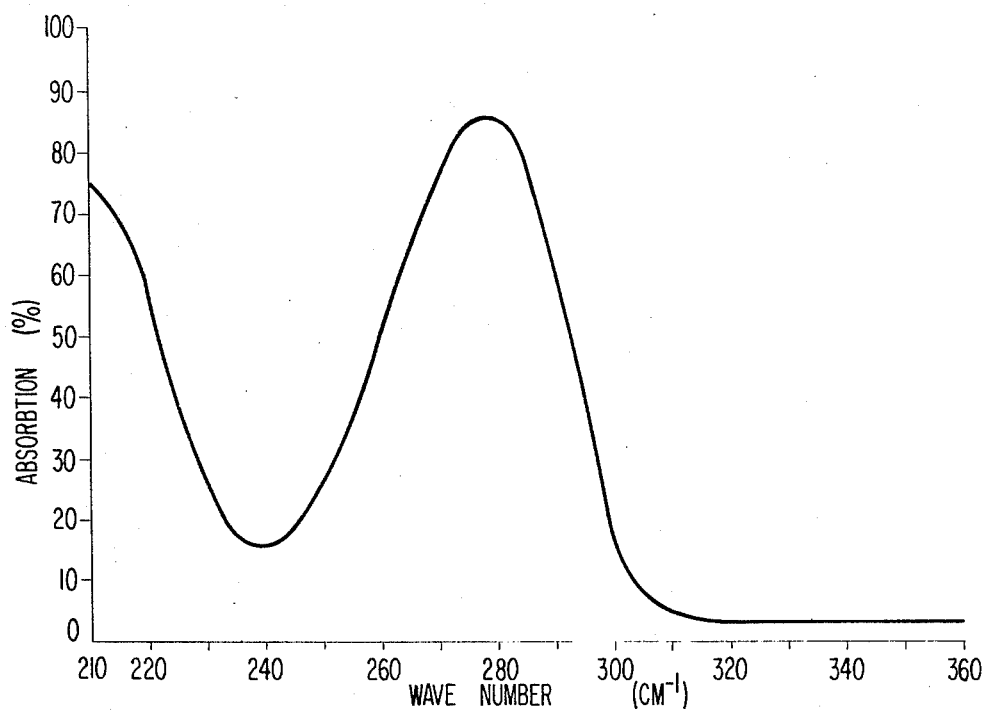
FIG. 3 is an UV absorption spectrum of 2',3'-O-sulfinyl-cytidine-5' phosphate.
Figure 4:
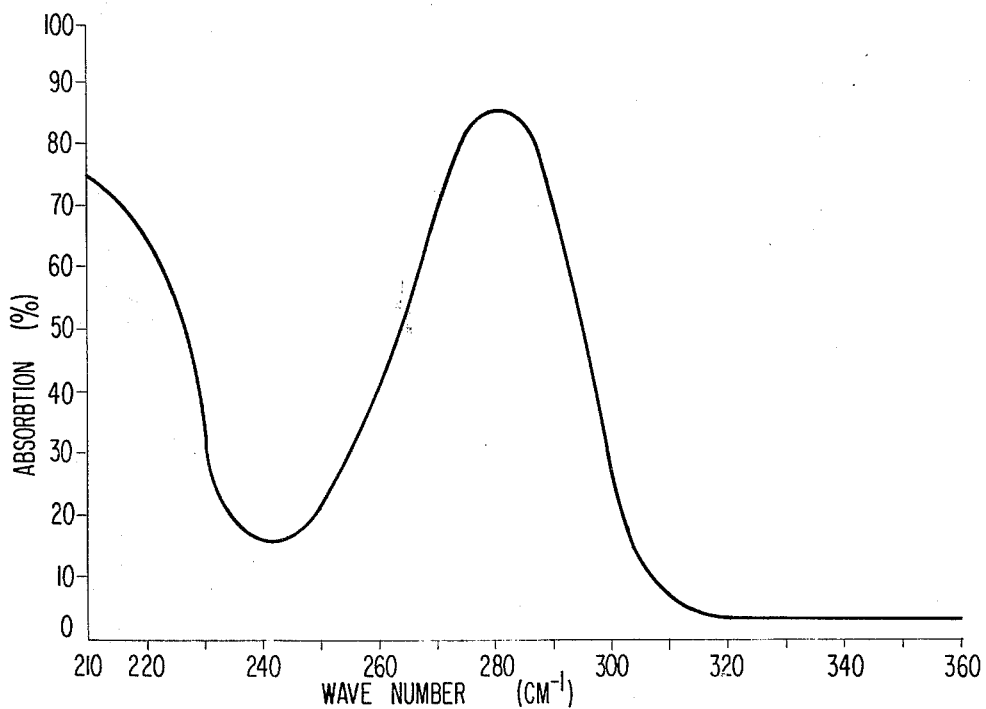
FIG. 4 is an UV absorption spectrum of cytidine-5'-phosphate as a reference.

2',3'-O-sulfinyl-cytidine-5'-phosphate is a novel compound previously not reported in literature and its IR and UV spectra are shown in FIGS. 1 and 3, respectively. Some of the characteristics of 2',3'-O-sulfinyl-cytidine-5'-phosphate obtained as described in Example 1 hereinafter given in detail are as follows:

1. Elemental Analysis values are as follows and are well consistent with the theoretical values of 2',3'-O-sulfinyl-cytidine-5'-phosphate.

Found(%): C, 29.40; H, 3.20; N, 11.61; S, 8.45.
Calcd. for $C_9H_{12}N_3O_9PS$ (%): C, 29.25; H, 3.25; N, 11.37; S, 8.67.

2. In the IR absorption spectrum of 2',3'-O-sulfinyl-cytidine-5'-phosphate as shown in FIG. 1, a characteristic absorption based on >S=O is observed at 990–1010 cm$^{-1}$ and an intense characteristic absorption of a sulfite ester

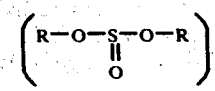

is observed at 1200–1220 cm$^{-1}$.

3. In the UV absorption spectrum of 2',3'-O-sulfinyl-cytidine-5'-phosphate as shown in FIG. 3, the maximum absorption wavelength (λ max) is 279 nm (at pH 2.0) and the minimum absorption wavelength (λ min) is 240 nm (at pH 2.0).

4. In paper chromatography (developed with n-butanol: acetic acid:water = 4:15 by volume), a single spot having an $R_f$ value of 0.30 is observed (the $R_f$ value of the starting cytidine-5'-phosphate is 0.10).

5. Melting Point: 196 to 200° C (with decomposition).

As described above, 2',3'-O-sulfinyl-cytidine-5'-phosphate of the present invention is useful as a starting material for the synthesis of 2,2'-anhydrocytidine-5'-phosphate. That is, the desired 2,2'-anhydrocytidine-5'-phosphate can be prepared easily by heating the above described 2',3'-O-sulfinyl-cytidine:5'-phosphate intermediate in a solvent such as water, an aprotonic polar solvent or a cyclic tertiary amine at a temperature from about 40° to about 150° C, preferably 70° to 140° C.

The solvent which can be used in the above reaction include water, aprotonic polar solvents such as dimethylformamide, dimethylacetamide, dimethylsulfoxide, hexamehtylphosphoramide, and cyclic tertiary amines such as pyridine, α-picoline, β-picoline, γ-picoline and 2,6-lutidine.

These reaction solvents can be generally used in an amount in the range of from at least about 5 liters, preferably about 10 to 30 liters, per mole of the starting 2',3'-O-sulfinyl-cytidine-5'-phosphate. When the amount of the reaction solvent is less than about 5 liters per mole of 2',3'-O-sulfinyl-cytidine-5'-phosphate, the mixing of the reaction solution becomes to be difficult and in addition the reaction time tends to be prolonged. On the other hand, the use of a large amount of the reaction solvent generally does not adversely affect the reaction and the desired product, but is not preferable from the standpoint of economy.

The time required for the reaction generally varies depending upon such factors as temperature used, concentration of the reactant in the reaction system and the like. It has been found, however, that the reaction time in the range of from about 1 to 15 hours is generally sufficient. It is to be noted, however, that the reaction at a relatively high temperature for a long period of time tends to cause undesirable decomposition of the product thereby increasing the formation of undesirable by-products.

The product, 2,2'-anhydrocytidine-5'-phosphate can be isolated from the reaction mixture as crystals by usual procedures which are well known to one skilled in the art. For examle, the product can be isolated by distilling off the reaction solvent from the reaction mixture, dissolving the thus obtained residue in hot water and adding a polar organic solvent to the solution to precipitate the product.

The present invention is further illustrated by the following Examples but they are given for illustrative purposes only and are not to be construed as limiting the scope of the present invention. Unless otherwise indicated, all parts, percents, ratios and the like are by weight.

EXAMPLE 1

300 ml of thionyl chloride (4.1 moles) and 240 ml of pyridine (3.0 moles) were added to 1 l of acetonitrile, and 323 g (1.0 mole) of cytidine-5'-phosphate was added to the mixture followed by mixing. After allowing the mixture to react for about 1 hour, the reaction mixture was mixed with 1.5 l of ice-water to hydrolyze any unreacted thionyl chloride. The resulting reaction mixture was adjusted to a pH of 2.3 with sodium bicarbonate and maintained overnight at a temperature of 0° to 5° C. Then, the reaction product was precipitated from the reaction mixture while stirring. The precipitated crystals were collected by filtration, washed thoroughly with cold water and further with cold methanol and dried under reduced pressure at room temperature to obtain 312 g (83.4% yield) of 2',3'-O-sulfinyl-cytidine-5'-phosphate having a purity of 98.6%. 148 g (0.4 moles) of the 2',3'-O-sulfinyl-cytidine-5'-phosphate obtained by the above reaction was added to 20 l of water and the mixture was allowed to react while stirring and heating at a temperature of 80° C for 9 hours. The resulting reaction mixture which contained 2,2'-anhydrocytidine-5'-phosphate in a yield of 83.0% was subjected to distillation under reduced pressure to remove the solvent and then concentrated to dryness. The residue thus obtained was dissolved in 4 l of warm water. Insoluble materials were removed by filtration and the filtrate was added to 400 ml of ethanol. The product was then precipitated from the resulting mixture while maintaining at a temperature of 0° to 5° C with stirring. The precipitated white crystals were collected by filtration, washed with cold 50% aqueous ethanol and dried under reduced pressure to obtain 82.2 g (66.0% yield) of crystalline 2,2'-anhydrocytidine-5' -phosphate ½ hydrate in a purity of 99.5%. The product thus obtained had the following characteristics:

Melting Point: 203° – 204° C (with decomposition).
U.V. $\lambda_{max}^{pH\ 1-7}$:232, 263, 283(sh) nm. Elemental Analysis:

Found (%): C, 34.27; H, 4.10; N, 13.33. Calcd. for $C_9H_{12}O_7N_3P \cdot \frac{1}{2}H_2O$ (%): C, 34.40; H, 4.17; N, 13.37

EXAMPLE 2

438 ml (6.0 moles) of thionyl chloride and 400 ml of γ-picoline (4.0 moles) were added to 1.0 l of tetrahydrofuran, and 323 g (1.0 mole) of cytidine 5'-phosphate was added to the mixture while maintaining at a temperature of 25° C. After allowing the mixture to react for about 1 hour at a temperature of 25° C while stirring, the reaction mixture was mixed with 1 l of ice-water to hydrolyze any unreacted thionyl chloride. The resulting reaction mixture was allowed to stir overnight at a temperature of 0 to 5° C to precipitate crystals. The precipitated crystalline product was collected by filtration, washed with cold water and further with cold methanol and dried under reduced pressure at room temperature to obtain 273 g (71.8% yield) of white crystalline 2',3'-O-sulfinyl-cytidine-5'-phosphate having a purity of 97.0%. 148 g (0.4 moles) of the thus obtained 2',3'-O-sulfinyl-cytidine-5'-phosphate was added to 4 l of dimethylformamide and the mixture was allowed to react while stirring and heating at a temperature of 90° C for 5 hours. The resulting reaction mixture which contained 2,2'-anhydrocytidine-5'-phosphate in a yield of 85.7% was then worked up in the same manner as described in Example 1 to obtain 8.13 g (65.4% yield) of white crystalline 2,2'-anhydrocytidine-5'-phosphate having a purity of 99.4%.

EXAMPLE 3

365 ml (5.0 moles) of thionyl chloride and 250 ml (2.5 mole) of α-picoline were added to 1.5 l of nitromethane, and 323 g (1.0 mole) of cytidine 5'-phosphate was added to the mixture while maintaining at a temperature of 30° C. The resulting mixture was then reacted for about 1 hour while stirring. The reaction mixture was then subjected to distillation at a temperature below 30° C under reduced pressure to remove nitrobenzene and any unreacted thionyl chloride. The residue thus obtained was mixed with 2 l of ice-water thereby precipitating white crystals. 1 l of acetone was added to the mixture which was then allowed overnight to precipitate crystals while maintaining at a temperature of 0° to 5° C. The precipitated crystals were then worked up in the same manner as described in Example 1 to obtain 292 g (77.0% yield) of white crystalline 2',3'-O-sulfinyl-cytidine-5'-phosphate having a purity of 97.3%. 148 g (0.4 moles) of the 2',3'-O-sulfinyl-cytidine-5'-phosphate obtained by the above reaction was added to 30 l of pyridine, and the mixture was allowed to react while stirring and heating at a refluxing temperature for 3 hours. The resulting reaction mixture which contained 2,2'-anhydrocytidine-5'-phosphate in a yield of 78.1% was subjected to distillation under reduced pressure to remove the solvent to dryness, and the residue was dissolved in 2 l of water. The solution was then adjusted to a pH of 2.5 with 6N HCl and treated with 2 g of activated carbon at a temperature of 60° C for 1 hour to decolorize the mixture. The mixture was filtered to remove the activated carbon, and the filtrate was concentrated to a volume of 350 ml. 250 ml of iso-propanol was added to the concentrated filtrate and the mixture was stored overnight at a cool place while stirring to precipitate crystals. The precipitated white crystals were collected by filtration, washed with a cold 50% aqueous ethanol and dried to obtain 74.6 g (61.3% yield) of white crystalline 2,2'-anhydrocytidine-5'-phosphate having a purity of 37.2%.

EXAMPLE 4

265 ml (3.6 moles) of thionyl chloride was added to 4.0 l of pyridine, and 323 g (1.0 mole) of cytidine 5'-phosphate was added to the mixture while stirring and cooling at a temperature of −12° C. After allowing the mixture to react for 3 hours, 10 l of diethyl ether was added to the reaction mixture whereby a viscous material precipitated. The supernatant was removed and the precipitated viscous material was poured into 2 l of ice-water followed by addition of 2 l of methanol. The mixture was then stirred overnight while maintaining at a temperature of 0° to 5° C to precipitate crystals. The precipitated crystals were then worked up in the same manner as described in Example 1 to obtain 294 g (76.3% yield) of white crystalline 2',3'-O-sulfinyl-cytidine 5'-phosphate having a purity of 95.8%. 148 g (0.4 moles) of the 2',3'-O-sulfinyl-cytidine-5'-phosphate obtained by the above reaction was added to 10 l of dimethylsulfoxide and the mixture was allowed to react for 4 hours while stirring and heating at a temperature of 130° C. The resulting reaction mixture which contained 2,2'-anhydrocytidine-5'-phosphate in a yield of 83.3% was then worked up in the same manner as described in Example 1 to obtain 79.5 g (64.6% yield) of 2,2'-anhydrocytidine-5'-phosphate having a purity of 98.4%.

EXAMPLE 5

727 ml (10 moles) of thionyl choride and 4.0 moles of 2,6-lutidine were added to 500 ml of dioxane, and 323 g (1.0 mole) of cytidine 5'-phosphate was added to the mixture while stirring and cooling at a temperature of 15° C. After allowing the mixture to react for about 2 hours, the reaction mixture was worked up in the same manner as described in Example 3 to obtain 298 g (79.0% yield) of white crystalline 2',3'-O-sulfinyl-cytidine-5'-phosphate having a purity of 97.8%. 148 g (0.4 moles) of the 2',3'-O-sulfinyl-cytidine-5'-phosphate obtained by the above reaction was added to 20 l of γ-picoline and the mixture was allowed to react while stirring and heating at a temperature of 100° C for 7 hours. The resulting reaction mixture which contained 2,2'-anhydrocytidine-5'-phosphate in a yield of 75.9% was worked up in the same manner as described in Example 3 to obtain 76.8 g (62.8% yield) of 2,2'-anhydrocytidine-5'-phosphate having a purity of 98.0%.

EXAMPLE 6

364 ml (5 moles) of thionyl chloride and 300 ml (3 moles) of β-picoline were added to 2 l of dimethylformamide, and 323 g (1.0 mole of cytidine 5'-phosphate was added to the mixture while stirring and colling at a temperature of 0°C. After allowing the mixture to react for about 2 hours, 10 l of benzene was added to the reaction mixture which was then stirred and allowed to stand to separate two layers. The upper layer was removed, and the lower layer as a viscous liquid was poured slowly into 2 l of ice-water. The mixture was adjusted to a pH of 2 and 2 l of ethanol was added to the mixture followed by stirring overnight in a cool room at a temperature below 5° C to precipitate crystals. The precipitated crystals were then worked up in the same manner as described in Example 1 to obtain 310 g (80.3% yield) of 2',3'-O-sulfinyl-cytidine-5'-phosphate having a purity of 95.5%. 148 g (0.4 moles) of the 2',3'-O-sulfinyl-cytidine-5'-phosphate obtained by the above reaction was added to a mixture of 5 l of water and 5 l of dimethylformamide, and the resulting mixture was reacted while stirring and heating at a temperature of 100° C for 6 hours. The resulting reaction mixture which contained 2,2'-anhydrocytidine-5'-phosphate in a yield of 87.5% was worked up in the same manner as described in Example 1 to obtain 83.0 g (66.9% yield) of crystalline 2,2'-anhydrocytidine-5'-phosphate having a purity of 99.2%.

EXAMPLE 7

220 ml (3 moles) of thionyl chloride and 270 ml (2.7 moles) of γ-picoline were added to 1 l of propionitrile, and 323 g (1 mole) of cytidine-5'-phosphate was added to the mixture while cooling at a temperature of 5° C and stirring. After allowing the mixture to react for about 15 hours, the reaction mixture was worked up in the same manner as described in Example 1 to obtain 310 g (81.5% yield) of white crystalline 2',3'-O-sulfinyl-cytidine-5'-phosphate having a purity of 9.4%. The thus obtained 2',3'-O-sulfinyl-cytidine-5'-phosphate was then worked up in the same manner as described in Example 4 but using 8 l of hexamethylphosphoramide in place of dimethylsulfoxide to obtain 74.5 g (60.6% yield) of crystalline 2,2'-anhydrocytidine-5'-phosphate having a purity of 98.3%.

EXAMPLE 8

300 ml (4.1 moles) of thionyl chloride and 280 ml (3.5 moles) of pyridine were added to 800 ml of nitroethane, and 323 g (1 mole) of cytidine-5'-phosphate was added to the mixture while stirring and cooling at a temperature of 5° C. After allowing the mixture to react for about 2 hours, the reaction mixture was worked up in the same manner as described in Example 3 to obtain 289 g (75.9% yield) of 2',3'-O-sulfinyl-cytidine 5'-phosphate having a purity of 97.0 %. 148 g (0.4 moles) of 2',3'-O-sulfinyl-cytidine-5'-phosphate obtained by the above reaction was added to 8 l of dimethylacetamide, and the mixture was allowed to react for 5 hours while stirring and heating at a temperature of 120° C. The resulting reaction mixture which contained 2,2'-anhydrocytidine-5'-phosphate in a yield of 80.2% was then worked up in the same manner as described in Example 1 to obtain 79.3 g (65.0% yield) of crystalline 2,2'-anhydrocytidine-5'-phosphate having a purity of 97.6%.

Example 9

300 ml (4.1 moles) of thionyl chloride and 240 ml (3.0 moles) of pyridine were added to 2 l of hexamethylphosphorus amide, and 323 g (1.0 mole) of cytidine-5'-phosphate was added to the mixture. After allowing the mixture to react for about 2 hours, the resulting reaction mixture was worked up in the same manner as described in Example 6 to obtain 299 g (78.0% yield) of 2',3'-O-sulfinyl-cytidine-5'-phosphate having a purity of 96.2%. 148 g (0.4 moles) of 2',3'-O-sulfinyl-cytidine-5'-phosphate was added to 25 l of 2.6 - lutidine, and the mixture was allowed to react while stirring and heating at a temperature of 100° C for 7 hours. The resulting reaction mixture which contained 2,2'-anhydrocytidine-5'-phosphate in a yield of 73.8% was worked up in the same manner as described in Example 3 to obtain 75.5 g (62.9% yield) of crystalline 2,2'-anhydrocytidine-5'-phosphate having a purity of 96.3%.

Example 10

300 ml (4.1 moles) of thionyl chloride was added to 3 l of γ-picoline, and 323 g (1.0 mole) of cytidine 5'-phosphate was added to the mixture while stirring and cooling at a temperature of 0° C. After allowing the mixture to react for about 1 hour, the resulting reaction mixture was worked up in the same manner as described in Example 4 to obtain 300 g (78.8% yield) of 2',3'-O-sulfinyl-cytidine-5'-phosphate having a purity of 97.1%. 148 g (0.4 moles) of the 2',3'-O-sulfinyl-cytidine-5'-phosphate obtained by the above reaction was then added to 15 l of picoline (a mixture of α,β and γ-picoline isomers), and the resulting mixture was allowed to react while stirring and heating at a temperature of 110° C for 8 hours. The reaction mixture thus obtained containing 2,2'-anhydrocytidine-5'-phosphate in a yield of 76.6% was then worked up in the same manner as described in Example 3 to obtain 77.4 g (63.7% yield) of crystalline 2,2'-anhydrocytidine-5'-phosphate having a purity of 97.2%.

While the invention has been described in detail with reference to specific embodiments thereof, it will be apparent to one skilled in the art that various changes and modifications can be made therein without departing from the spirit and scope thereof.

What is claimed is:

1. 2',3'-O-Sulfinyl-cytidine-5'-phosphate represented by the formula

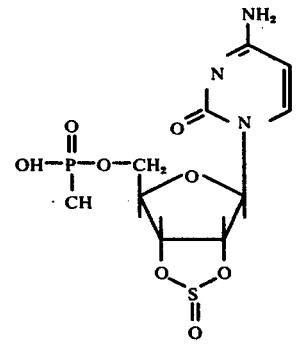

* * * * *